United States Patent
Goto

(10) Patent No.: US 9,487,543 B2
(45) Date of Patent: Nov. 8, 2016

(54) SILICONE COMPOUND HAVING A RADICAL-POLYMERIZABLE GROUP AND A METHOD FOR THE PREPARATION THEREOF

(71) Applicant: SHIN-ETSU CHEMICAL CO., LTD., Tokyo (JP)

(72) Inventor: Tomoyuki Goto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/885,428

(22) Filed: Oct. 16, 2015

(65) Prior Publication Data
US 2016/0108066 A1    Apr. 21, 2016

(30) Foreign Application Priority Data
Oct. 17, 2014 (JP) .................... 2014-212682

(51) Int. Cl.
| | |
|---|---|
| C07F 7/10 | (2006.01) |
| C07F 7/08 | (2006.01) |
| C07F 7/18 | (2006.01) |
| C08F 230/08 | (2006.01) |
| G02B 1/04 | (2006.01) |

(52) U.S. Cl.
CPC ........... *C07F 7/0854* (2013.01); *C07F 7/0889* (2013.01); *C07F 7/1836* (2013.01); *C07F 7/1868* (2013.01); *C07F 7/1892* (2013.01); *C08F 230/08* (2013.01); *G02B 1/041* (2013.01); *G02B 1/043* (2013.01)

(58) Field of Classification Search
CPC ....................................... C07F 7/08
USPC ........................................ 556/421
IPC ......................................... C07F 7/08
See application file for complete search history.

(56) References Cited

U.S. PATENT DOCUMENTS

| | | |
|---|---|---|
| 3,808,178 A | 4/1974 | Gaylord |
| 4,927,951 A | 5/1990 | Kabeta et al. |
| 2005/0176911 A1 | 8/2005 | Zanini et al. |

FOREIGN PATENT DOCUMENTS

| | | | |
|---|---|---|---|
| CA | 2 622 733 A1 | 8/2009 | |
| CA | 2622733 A1 * | 8/2009 | ............ G02B 1/043 |
| JP | 10170874 A * | 6/1998 | |
| JP | 2007-186709 A | 7/2007 | |
| JP | 2007-526364 A | 9/2007 | |
| JP | WO 2011116206 A1 * | 9/2011 | ............ C08G 77/14 |
| WO | WO 2011/116206 A1 | 9/2011 | |
| WO | WO 2012/130956 A1 | 10/2012 | |

OTHER PUBLICATIONS

Akiyoshi et al., "Contact Lens Materials", Encyclopedia of Advanced Biomaterials, published in Jun. 2012, Chapter V, Paragraph V, pp. 528-533.
Database CA [Online] Chemical Abstracts Service, Columbus, Ohio, US; 1998, Saito et al. "Plastic moldings having high transparency, permeability, and mechanical properties," XP002754952.
Extended European Search Report issued Mar. 15, 2016, in European Patent Application No. 15189692.5.

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

A silicon compound that contains a radical-polymerizable group. The silicone compound is liquid at room temperature and has good handling properties, has excellent reactivity, and provides a cured product having excellent oxygen permeability. The silicone compound is represented by formula (1):

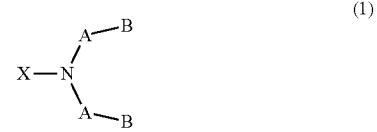

wherein each A is, independently, a divalent hydrocarbon or halohydrocarbon group having 1 to 6 carbon atoms, each B is, independently, a monovalent organosilicone residue having 2 to 20 silicon atoms, and X is a specified type of moiety comprising a monovalent radical-polymerizable group. A method for preparing the silicone compound. The silicone compound is useful for ophthalmic device compositions, coatings, and cosmetic compositions such as skin care cosmetics, hair care cosmetics, antiperspirants, deodorants, makeup cosmetics, and ultraviolet protection cosmetics.

8 Claims, No Drawings

SILICONE COMPOUND HAVING A RADICAL-POLYMERIZABLE GROUP AND A METHOD FOR THE PREPARATION THEREOF

CROSS REFERENCE

This application claims the benefits of Japanese Patent application No. 2014-212682 filed on Oct. 17, 2014, the contents of which are hereby incorporated by reference.

FIELD OF THE INVENTION

The present invention relates to a silicone compound having a radical-polymerizable group at a terminal and a method for the preparation of the silicone compound. Specifically, the present silicone compound has an excellent oxygen permeability and good handling properties at room temperature.

Silicone hydrogels for contact lens materials were developed. Encyclopedia of Advanced Biomaterials, Non-Patent Literature 1, describes that a silicone compound such as polydimethylsiloxane, which has a polymerizable group, is as a raw material to improve oxygen permeability, flexibility and mechanical strength of lenses. U.S. Pat. No. 3,808,178 describes 3-[tris(trimethylsiloxy)silyl]propyl methacrylate (TRIS) as a silicone monomer used for ophthalmic devices. A silicone hydrogel is prepared by copolymerization of a hydrophilic monomer and a polymerizable silicone compound. Therefore, it is important that a polymerizable silicone compound is compatible with a hydrophilic monomer. However, TRIS has poor compatibility with a hydrophilic monomer. Non-patent literature 1, Japanese Patent Application Laid-Open No. 2007-186709 and Japanese National Phase Publication No. 2007-526364 describe a method for improving compatibility of a polymerizable silicone compound with a hydrophilic monomer by introducing a polar functional group such as an amide, urethane or hydroxyl group into the polymerizable silicone compound.

WO2012/130956 describes a composition for preparing an ophthalmic lens, comprising units derived from 3-[tris(trimethylsiloxy)silyl]propyl acrylamide. 3-[tris(trimethylsiloxy)silyl]propyl acrylamide (TRIS-A) is often used as one of monomer components for contact lens materials because of its good UV curability on account of the radical-polymerizable acryl group. However, TRIS-A has a melting point of approximately 50 degrees C. and is solid at room temperature, so that its handling properties is bad at room temperature.

PRIOR LITERATURES

Patent Literature 1: U.S. Pat. No. 3,808,178
Patent Literature 2: Japanese Patent Application Laid-Open No. 2007-186709
Patent Literature 3: Japanese National Phase Publication No. 2007-526364
Patent Literature 4: WO2012/130956
Non-Patent Literature 1: Encyclopedia of Advanced Biomaterials, Akiyoshi et. al., published in June, 2012, Chapter V, Paragraph V, pages 528-533, "CONTACT LENS MATERIALS"

One of the purposes of the present invention is to provide a radical-polymerizable group-containing silicone compound which is liquid and has good handling properties at room temperature, has excellent reactivity and provides a cured product having an excellent oxygen permeability.

The inventor has found a silicone compound represented by the following formula (1). Thus, the present invention provides a silicone compound represented by the following formula (1):

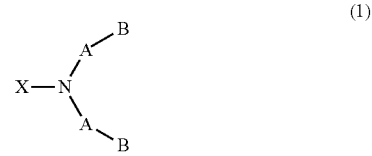
(1)

wherein A is, independently of each other, a substituted or unsubstituted, linear or branched, divalent hydrocarbon group having 1 to 6 carbon atoms, B is, independently of each other, a monovalent organosilicone residue having 2 to 20 silicon atoms, and X is a monovalent radical-polymerizable group or a monovalent group comprising said monovalent radical-polymerizable group.

Further, the present invention provides a method for preparing the silicone compound.

The present silicone compound is liquid and has good handling properties at room temperature and provides a cured product having an excellent oxygen permeability. Further, the silicone compound has good reactivity.

DETAILED DESCRIPTION OF THE INVENTION

The present invention will be described below in detail.
The present invention provides a silicone compound represented by the following formula (1):

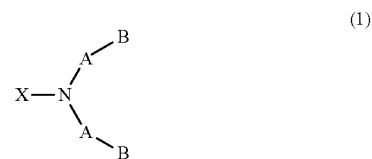
(1)

wherein A is, independently of each other, a substituted or unsubstituted, linear or branched, divalent hydrocarbon group having 1 to 6 carbon atoms, B is, independently of each other, a monovalent organosilicone residue having 2 to 20 silicon atoms, and X is a monovalent radical-polymerizable group or a monovalent group comprising said monovalent radical-polymerizable group.

The present silicone compound is characterized in that the radical-polymerizable group X and the siloxane chain B are bound with each other via a nitrogen atom, which nitrogen atom the two siloxane chains are bound to. On account of this structure, the present silicone compound has the excellent oxygen permeability. The present silicone compound is liquid at room temperature and, therefore, has good handling properties. This is because no hydrogen atom is bound to the nitrogen atom which the radical-polymerizable group X and the siloxane chains B are bound to.

In the aforesaid formula (1), A is, independently of each other, a substituted or unsubstituted, linear or branched, divalent hydrocarbon group having 1 to 6 carbon atoms. Examples of the divalent hydrocarbon group include an ethylene group, a 1,3-propylene group, a 1-methylpropylene group, a 1,1-dimethylpropylene group, a 2-methylpropylene group, a 1,2-dimethylpropylene group, a 1,1,2-trimethylpropylene group, a 1,4-butylene group, a 2-methyl-1,4-butylene group, a 2,2-dimethyl-1,4-butylene group, a 3-methyl-1,4-butylene group, a 2,3-dimethyl-1,4-butylene group, a 2,2,3-trimethyl-1,4-butylene group, a 1,5-pentylene group and a 1,6-hexanylene group, and these groups where a part or the whole of their hydrogen atoms bonding to carbon atoms are replaced with a halogen atom(s) such as a chlorine atom and a fluorine atom, such as halogen-substituted alkylene groups. Among these, preferred is a linear divalent hydrocarbon group having 2 to 5 carbon atoms.

In the aforesaid formula (1), X is a monovalent radical-polymerizable group or a monovalent group the comprising said monovalent radical-polymerizable group. Examples of the radical-polymerizable group include a (meth)acryl group, a styryl group, an indenyl group, an alkenyl group, a cycloalkenyl group, a norbornyl group, and a conjugated or unconjugated alkadiene group. For instance, X is preferably the groups represented by the following formula (3) or (4).

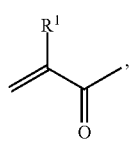

(3)

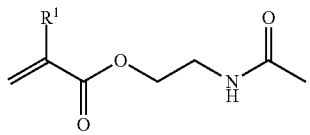

(4)

wherein $R^1$ is a hydrogen atom or a methyl group. A hydrogen atom is preferable in view of reactivity.

In the aforesaid formula (1), B is, independently of each other, a monovalent organosilicone residue having 2 to 20 silicon atoms, preferably 2 to 10 silicon atoms. The silicone residue may have a linear, ranched, or cyclic structure. Examples of B include an organopolysiloxane residue represented by the following formula (2)

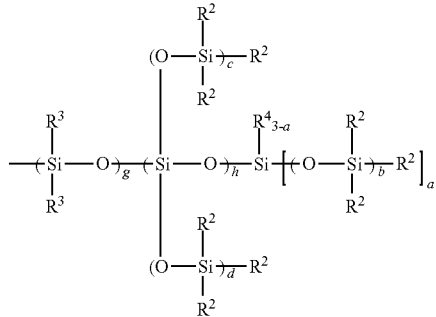

(2)

wherein $R^2$, $R^3$ and $R^4$ are, independently of each other, an alkyl group having 1 to 10 carbon atoms or an aryl group having 6 to 12 carbon atoms, b is an integer of from 1 to 3, c is an integer of from 1 to 3, d is an integer of from 0 to 3, g is an integer of from 0 to 10, h is an integer of from 0 to 2, and a is an integer of from 0 to 3, provided that not all of a, h and g are zero.

In particular, preferred is the structure represented by the following formula, thus the aforesaid formula (2) with g being zero and h being zero.

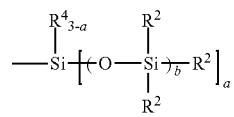

wherein a is 2 or 3, particularly 3, and b is an integer of from 1 to 3, preferably 1 or 2, particularly 1. $R^2$ and $R^4$ are as defined above.

In particular, the silicone residue represented by the following formula is preferable in view of their compatibility with the other monomer components.

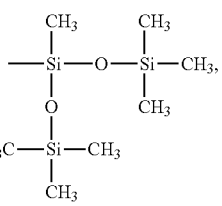
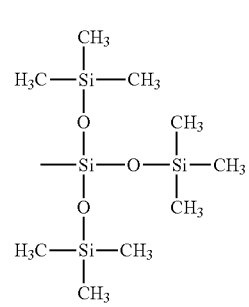

The aforesaid silicone compound represented by the formula (1) is preferably such represented by the following formula (5) or (6).

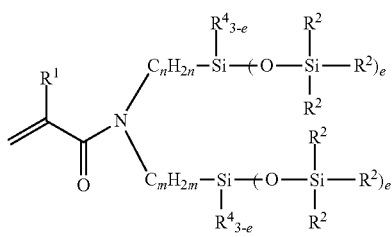

(5)

wherein $R^1$ is a hydrogen atom or a methyl group, preferably a hydrogen atom, $R^2$ and $R^4$ are, independently of each other, an alkyl group having 1 to 10 carbon atoms, n is an integer of from 1 to 6, m is an integer of from 1 to 6, and e is, independently of each other, 1, 2 or 3, preferably 2 or 3, particularly 3.

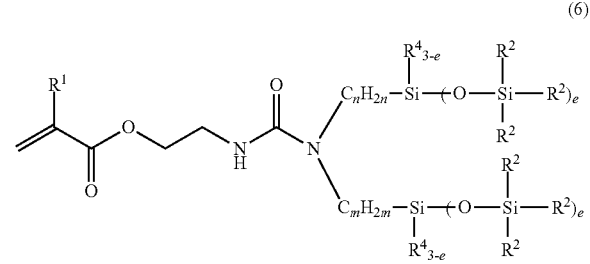

(6)

wherein $R^1$ is a hydrogen atom or a methyl group, preferably a hydrogen atom, $R^2$ and $R^4$ are, independently of each other, an alkyl group having 1 to 10 carbon atoms, n is an integer of from 1 to 6, m is an integer of from 1 to 6, and e is, independently of each other, 1, 2 or 3, preferably 2 or 3, particularly 3.

In particular, the silicone compound represented by the following formula (5') or (6') is preferable.

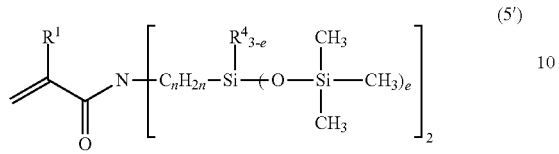
(5')

wherein $R^1$ is a hydrogen atom or a methyl group, preferably a hydrogen atom, $R^4$ is a methyl group, n is an integer of from 1 to 6, preferably 3, and e is 1, 2 or 3, preferably 2 or 3, particularly 3.

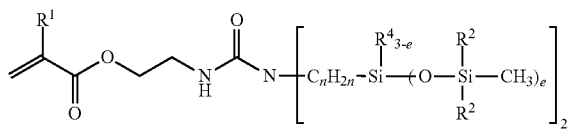
(6')

wherein $R^1$ is a hydrogen atom or a methyl group, preferably a hydrogen atom, $R^4$ is a methyl group, n is an integer of from 1 to 6, preferably 3, and e is 1, 2 or 3, preferably 2 or 3, particularly 3.

In particular, the acryl group-containing silicone compound whose $R^1$ is a hydrogen atom in the aforesaid formula is preferable in view of its curability, i.e. reactivity.

The present invention provides a method for preparing the silicone compound represented by the aforesaid formula (1). The method comprises a step of reacting a compound represented by the following formula (8):

$$Y—Z \quad (8)$$

wherein Y is a monovalent radical-polymerizable group or a monovalent group comprising said monovalent radical-polymerizable group, and Z is a halogen atom or a group which is reactive with an amine, with a compound represented by the following formula (9):

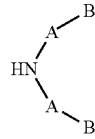
(9)

wherein A and B are as defined above.
A compound prepared in the aforesaid step is liquid at room temperature.

In the aforesaid formula (8), Y is a monovalent radical-polymerizable group or a monovalent group the comprising said monovalent radical-polymerizable group. Examples of the radical-polymerizable group include a (meth)acryl group, a styryl group, an indenyl group, an alkenyl group, a cycloalkenyl group, a norbornyl group, and a conjugated or unconjugated alkadiene group. For instance, the group represented by the following formula (3') or (4') is preferable.

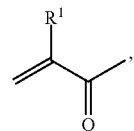
(3')

(4')

wherein $R^1$ is a hydrogen atom or a methyl group. A hydrogen atom is preferable in view of its reactivity.

In the aforesaid formula (8), Z is a halogen atom or a group which is reactive with an amine, including, for instance, halogenated alkyl groups, acid anhydride groups, ester groups, and isocyanate groups. The halogen atom includes chlorine, bromine and iodine atoms. In particular, a chlorine atom and isocyanate groups are preferred in view of reactivity and easiness of synthesis.

The compound represented by formula (8) is preferably (meth)acryl acid chloride, and ethyl (meth)acrylate isocyanate. In particular, acryl acid chloride, and ethyl acrylate isocyanate are preferred in view of reactivity, i.e., radical polymerizability.

For instance, the silicone compound represented by the following formula (5) may be prepared by the use of (meth)acryl acid chloride.

(5)

wherein $R^1$, $R^2$, $R^4$, n, m and e are as defined above.

In particular, the silicone compound represented by the formula (5) may be prepared by reacting (meth)acryl acid chloride represented by the following formula (10):

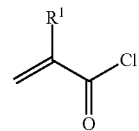
(10)

wherein $R^1$ is a hydrogen atom or a methyl group, with a compound represented by the following formula (11):

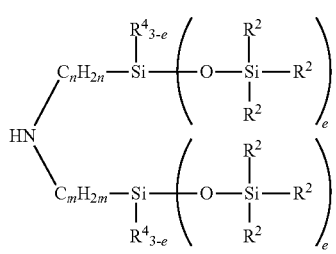

wherein $R^2$, $R^4$, n, m and e are as defined above.

Alternatively, the silicone compound represented by the following formula (6) may be prepared by the use of ethyl (meth)acrylate isocyanate.

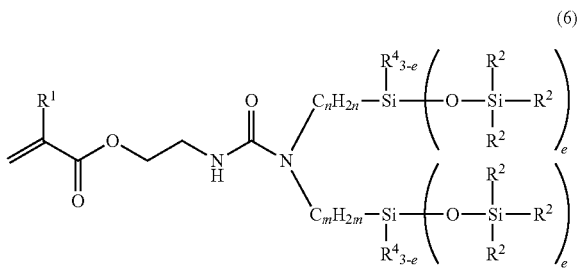

wherein $R^1$, $R^2$, $R^4$, n, m and e are as defined above.

In particular, the silicone compound represented by the formula (6) may be prepared by reacting a compound represented the following formula (12):

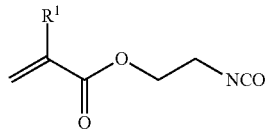

wherein $R^1$ is a hydrogen atom or a methyl group, with a compound represented by the following formula (13):

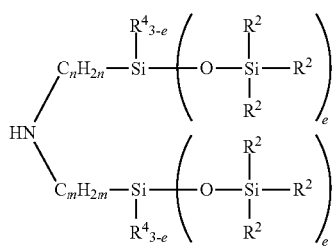

wherein $R^2$, $R^4$, n, m and e are as defined above.

In the aforesaid preparation process, an amount of the compound represented by formula (8), including those represented by formula (10) or (12), to be used may be properly decided. Preferably, 1 to 3 moles, more preferably 1.05 to 2 moles, of the compound represented by formula (8) are used per mole of the compound represented by formula (9), including those represented by formula (11) or (13). If the amount is less than the aforesaid lower limit, a large amount of the compound represented by formula (9) remains unreacted in a product, so that a purity of an envisaged product is worse. If the amount is larger than the aforesaid upper limit, costs may be higher.

The reaction may be carried out in an aqueous solution of an alkali metal salt or an alkaline earth metal salt. On account of the presence of an aqueous solution of an alkali metal salt or an alkaline earth metal salt, unreacted radical polymerizable group-containing compound and byproducts can be removed easily. Examples of the alkali metal salt and alkaline earth metal salt include lithium hydroxide, lithium carbonate, lithium hydrogen carbonate, sodium hydride, sodium hydroxide, sodium carbonate, sodium hydrogen carbonate, sodium borohydride, potassium hydride, potassium hydroxide, potassium carbonate, potassium hydrogen carbonate, dipotassium hydrogenphosphate, magnesium hydroxide, magnesium carbonate, calcium hydroxide, calcium carbonate, strontium hydroxide, strontium carbonate, barium hydroxide and barium carbonate. Among these, sodium hydroxide, sodium carbonate and potassium carbonate are preferred because of their availability, good handling properties, reactivity and stability of the compounds in a reaction system. Sodium carbonate is most preferred. An amount of sodium carbonate is preferably 1 mole or more, further preferably 2 moles or more, per mole of the compound having a radical-polymerizable group.

A reaction temperature is not particularly limited, but is preferably −20 to 60 degrees C., more particularly 0 to 20 degrees C. When the temperature is lower than −20 degrees C., a special apparatus is needed for reaction. When the temperature exceeds 60 degrees C., the radical-polymerizable group might cause polymerization.

A various type of polymerization inhibitors might be added to the reaction system in order to prevent the polymerization of the radical-polymerizable group. Examples of the polymerization inhibitors include hydroquinone, hydroquinone monomethyl ether, 4,4'-butylidene bis(6-t-butyl-m-crezol), 2,2'-methylene bis(4-methyl-6-t-butylpheol), 2,2'-methylene bis(4-ethyl-6-t-butylpheol), 2,6-di-t-butyl-p-crezol, 2,5-di-t-amyl-hydroquinoen, and 2,5-di-t-butyl-hydroquinoen, but not limited to these.

The present silicone compound may also be synthesized first by preparing the following alkoxysilane compound which a radical-polymerizable group has been introduced into

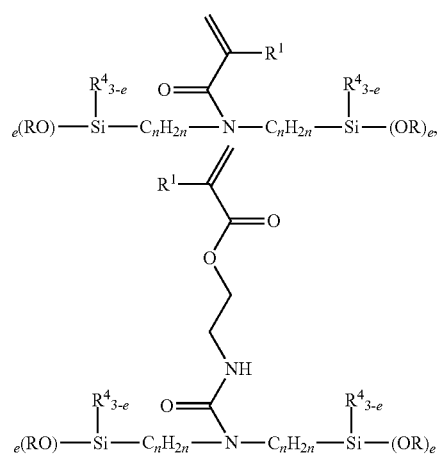

wherein $R^1$, $R^4$, n and e are as defined above and R is an alkyl group having 1 to 3 carbon atoms, then reacting this alkoxysilane compound with a silicone or silane compound having a halosilyl or alkoxysilyl group. However, the radical-polymerizable group introduced in advance might react to cause discoloration or thickening or gelation due to heating during the reaction process or a purification process. This problem might occur remarkably when the radical-polymerizable group is an acryl group, because an acryl group is highly reactive. Accordingly, in order to obtain the compound which is liquid at room temperature, it is better to introduce the radical-polymerizable group at the last stage, as stated above.

The present silicone compound has a low melting point and liquid at room temperature and, therefore, has good handling properties. Further, the present silicone compound provides a cured product having good oxygen permeability. Further, the present silicone compound has good compatibility with other monomer and has good reactivity. In particular, the compound whose radical-polymerizable group, X, is an acryl group has better curability, compared to the compounds whose radical-polymerizable group is a methacryl group, and is more preferable.

The other monomer which is polymerizable with the present silicone compound is not limited to particular ones and may be selected from conventional components depending on intended applications, such as, for instance, nitrogen atom-containing monomers such as N-vinylpyrrolidone, N,N-dimethylacrylamide and N-methyl-3-methylidenepyrrolidone; and hydrophilic monomers such as a methacrylic acid and hydroxyethyl(meth)acrylate.

A composition obtained by dissolving the present silicon compound and other monomer with each other is useful for, for instance, ophthalmic device compositions, coatings or cosmetic compositions. Examples of the cosmetics compositions include skin care cosmetics, hair care cosmetics, antiperspirants, deodorants, makeup cosmetics and ultraviolet protection cosmetics.

EXAMPLES

The present invention will be explained below in further detail with reference to a series of the Examples and the Comparative Examples, though the present invention is in no way limited to these Examples.

In the following descriptions, molecular structures were determined with nuclear magnetic resonance analysis, $^1$H-NMR. The apparatus used was $^1$H-NMR: AVANCE III, ex Bruker Biospin Co., Ltd.

Example 1

In a flask equipped with a thermometer, a dropping funnel, and a nitrogen inflow tube, were put 0.1 mole of a silicone compound represented by the following formula (I), 200 ml of hexane, and 170 g of an aqueous 10% solution of sodium carbonate, to which 1.2 moles of acrylic acid chloride were added dropwise at 5 degrees C. with stirring.

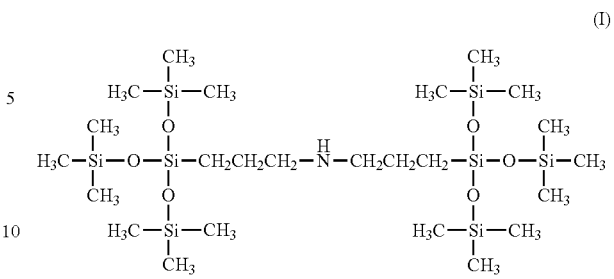

(I)

After the end of the dropping, the stirring was continued for 5 hours at room temperature, and an organic layer was washed with pure water. Subsequently, 0.008 gram of p-methoxyphenol, polymerization inhibitor, was added to the organic liquid after washed, which was then subjected to vacuum distillation at 5 torr, 60 degrees C. to distill off volatiles. The resultant product was liquid, pale yellow and transparent at room temperature (25 degrees C.). According to $^1$H-NMR analysis, the product was a compound represented by the following formula (II). The yield was 96.9%.

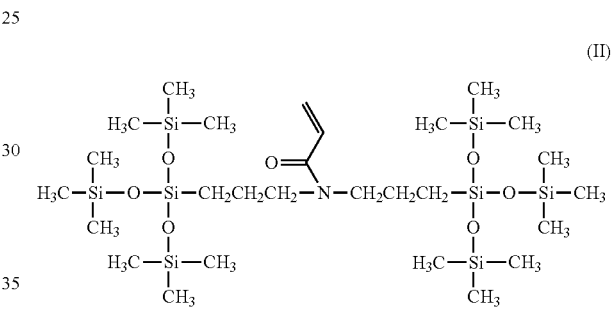

(II)

$^1$H-NMR spectrum was as follows.
$^1$H-NMR (400 MHz, CDCl$_3$): δ 0.06 (s, 54H), 0.33~0.50 (m, 4H), 1.49~1.67 (m, 4H), 3.18~3.38 (m, 4H), 5.61 (dd, 1H), 6.32 (ddd, 1H), 6.55 (dd, 1H)

Example 2

The procedures of Example 1 were repeated except that a compound represented by the following formula (III) was used instead of the compound represented by the formula (I) to obtain a product which was liquid, pale yellow and transparent at room temperature (25 degrees C.).

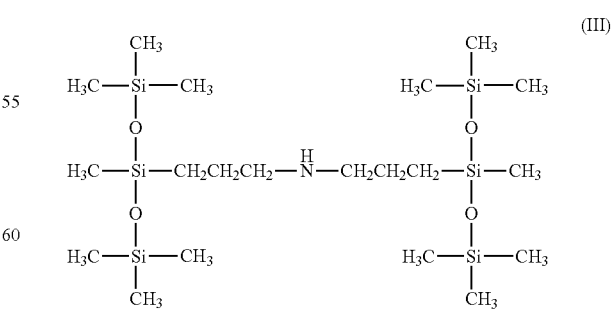

(III)

According to $^1$H-NMR analysis, the product was a compound represented by the following formula (IV). The yield was 97.3%.

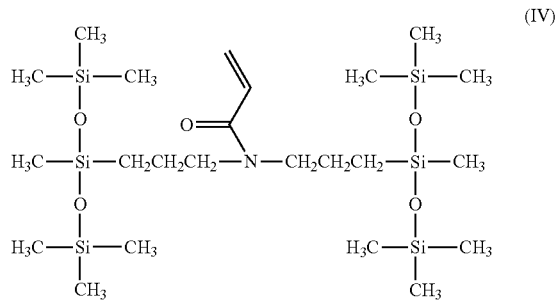

(IV)

¹H-NMR spectrum was as follows.

¹H-NMR (400 MHz, CDCl₃): δ 0.00 (s, 6H), 0.07 (s, 36H), 0.34~0.48 (m, 4H), 1.49~1.67 (m, 4H), 3.18~3.39 (m, 4H), 5.62 (dd, 1H), 6.32 (ddd, 1H), 6.53 (d d, 1H)

Example 3

The procedures of Example 1 were repeated except that 2-acryloyloxyethyl isocyanate was used instead of acrylic acid chloride to obtain a product which was liquid, pale yellow and transparent at room temperature (25 degrees C.). According to ¹H-NMR analysis, the product was a compound represented by the following formula (V). The yield was 95.2%.

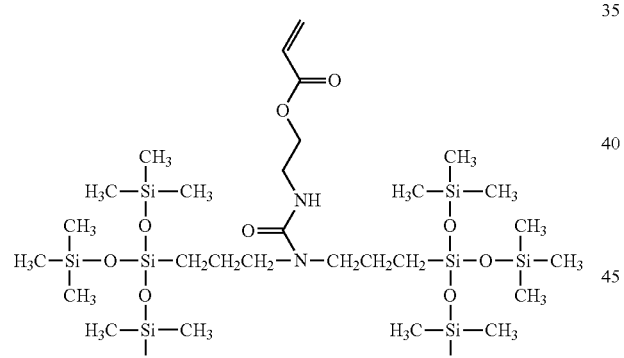

(V)

¹H-NMR spectrum was as follows.

¹H-NMR (400 MHz, CDCl₃): δ 0.07 (s, 54H), 0.34~0.45 (m, 4H), 1.49~1.68 (m, 4H), 3.08~3.20 (m, 4H), 3.49~3.5 9 (m, 2H), 4.18~4.28 (m, 2H), 4.72 (br, 1H), 5.82 (dd, 1H), 6.15 (ddd, 1H), 6.39 (dd, 1H)

Example 4

The procedures of Example 1 were repeated except that 2-methacryloyloxyethyl isocyanate was used instead of acrylic acid chloride to obtain a product which was liquid, pale yellow and transparent at room temperature (25 degrees C.). According to ¹H-NMR analysis, the product was a compound represented by the following formula (VI). The yield was 96.5%.

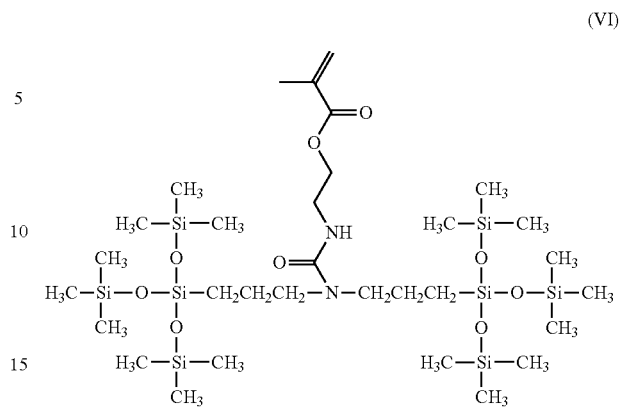

(VI)

¹H-NMR spectrum was as follows.

¹H-NMR (400 MHz, CDCl₃): δ 0.07 (s, 54H), 0.34~0.42 (m, 4H), 1.4 9~1.69 (m, 4H), 1.93 (m, 3H), 3.06~3.18 (m, 4H), 3.48~3.58 (m, 2H), 4.19~4.30 (m, 2H), 4.74 (br, 1H), 5.55 (s, 1H), 6.09 (s, 1H)

Example 5

The procedures of Example 2 were repeated except that methacrylic acid chloride was used instead of acrylic acid chloride to obtain a product which was liquid, pale yellow and transparent at room temperature (25 degrees C.). According to ¹H-NMR analysis, the product was a compound represented by the following formula (VII). The yield was 97.4%.

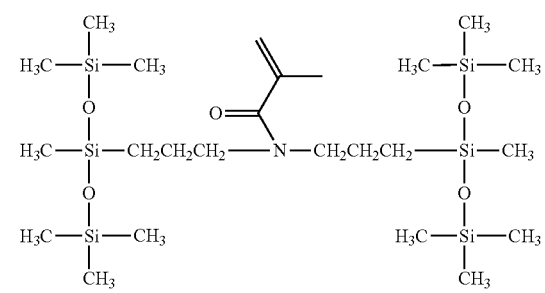

(VII)

¹H-NMR spectrum was as follows.

¹H-NMR (400 MHz, CDCl₃).: δ 0.00 (s, 6H), 0.07 (s, 36H), 0.34~0.48 (m, 4H), 1.49~1.67 (m, 4H), 1.96 (m, 3H), 3.16~3.37 (m, 4H), 5.05 (s, 1H), 5.20 (s, 1H)

Reference Example 1

In a flask equipped with a thermometer, a dropping funnel, and a nitrogen inflow tube, were put 0.1 mole of amine group-containing alkoxysilane represented by the following formula (IX), 200 ml of toluene, and 0.12 mole of triethylamine, to which 0.11 mole of acrylic acid chloride was added dropwise at 5 degrees C. with stirring.

(IX)

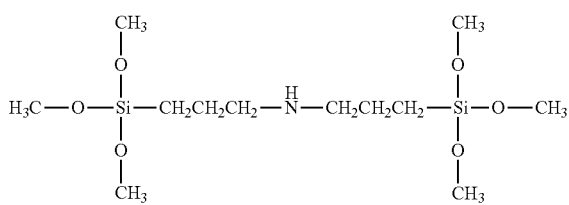

After the end of the dropping, the stirring was continued for 5 hours at room temperature, 0.3 ml of methanol was added and the stirring was continued for further 30 minutes. Then, an organic layer was washed with pure water. Subsequently, 0.008 gram of p-methoxyphenol, polymerization inhibitor, was added to the organic layer after washed, which was then subjected to vacuum distillation at 5 torr, 60 degrees C. to distill off volatiles. The resultant product was liquid and yellow. According to $^1$H-NMR analysis, the product was a compound represented by the following formula (X). The yield was 92.9%.

(X)

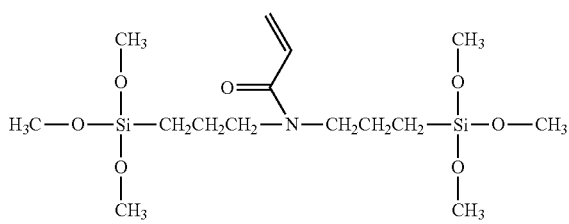

Subsequently, in a flask equipped with a thermometer, a dropping funnel, and a nitrogen inflow tube, were put 20 ml of water, 20 ml of methanol and 40 ml of hexane, to which a mixture of 0.03 mole of the aforesaid compound (X) and 0.27 mole of trimethylchlorosilane was added dropwise at 5 degrees C. After the end of the dropping, the stirring was continued for 3 hours at room temperature, an organic layer was washed with pure water. Subsequently, 0.003 gram of p-methoxyphenol, polymerization inhibitor, was added to the organic layer after washed, which was then subjected to vacuum distillation at 5 torr, 60 degrees C. to distill off volatiles. During the distillation, the liquid reaction product gelled.

Reference Example 2

The procedures of Reference Example 1 were repeated except that 2-acryloyloxyethyl isocyanate was used instead of acrylic acid chloride. During the distillation, the liquid reaction product gelled, as in Reference Example 1.

Comparative Example 1

Synthesis of 3-[tris(trimethylsiloxy)silyl]propyl acrylamide (TRIS-A)

The procedures of Example 1 were repeated except that [(CH$_3$)$_3$SiO)]$_3$Si(CH$_2$)$_3$—NH$_2$ was used instead of the compound represented by the aforesaid formula (1) to obtain a product which was white and solid at room temperature (25 degrees C.). According to $^1$H-NMR analysis, the product was a silicone compound represented by the following formula (VIII). The yield was 93.1%.

(VIII)

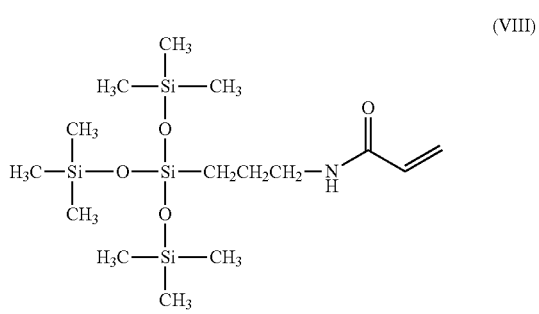

$^1$H-NMR spectrum was as follows.
$^1$H-NMR (400 MHz, CDCl$_3$): δ 0.09 (s, 27H), 0.45~0.50 (m, 2H), 1.59 (m, 2H), 3.32 (m, 2H), 5.58 (b r, 1H), 5.62 (dd, 1H), 6.06 (ddd, 1H), 6.25 (d d, 1H)

The states at room temperature (25 degrees C.) of the silicone compounds obtained in Examples 1 to 5 and Comparison Example 1 are as shown in Table 1.

TABLE 1

| | Ex. 1 | Ex. 2 | Ex. 3 | Ex. 4 | Ex. 5 | Com. Ex. 1 |
|---|---|---|---|---|---|---|
| State | liquid | liquid | liquid | liquid | liquid | solid |

The compound obtained in Comparison Example 1, 3-[tris(trimethylsiloxy)silyl]propyl acrylamide (TRIS-A), had a melting point of 51 degrees C., and was solid at room temperature (25 degrees C.). In contrast, the compounds according to the invention were liquid at room temperature (25 degrees C.) and, therefore, easy to handle.

Comparative Example 2

The procedures of Example 1 were repeated except that [(CH$_3$)$_3$SiO)]$_3$Si(CH$_2$)$_3$—NHC$_6$H$_{13}$ was used instead of the compound represented by the aforesaid formula (1) to obtain a product which was pale yellow and liquid at room temperature (25 degrees C.). According to $^1$H-NMR analysis, the product was a silicone compound represented by the following formula (XI). The yield was 91.0%.

(XI)

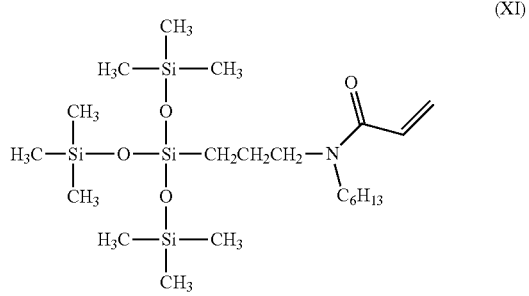

$^1$H-NMR spectrum was as follows.
$^1$H-NMR (400 MHz, CDCl$_3$): δ 0.09 (s, 27H), 0.35-0.46 (m, 2H), 0.85-0.93 (m, 3H), 1.23-1.36 (m, 6H), 1.12-1.52 (m, 4H), 3.21-3.33 (m, 2H), 3.33-3.40 (m, 2H), 5.63 (dd, 1H), 6.34 (ddd, 1H), 6.54 (dd, 1H)

[Preparation of a Cured Product]

In a reactor, put were 65 parts by mass of each of the compounds obtained Examples 1 to 5 and Comparison Example 1, 34 parts by mass of N,N-dimethylacrylamide, 1 part by mass of triethyleneglycol, and 0.5 part by mass of Darocure 1173, ex Chiba Speciality Chemicals, and mixed with stirring. The obtained mixture was deaerated, poured into a mold made of an ethylene-vinyl alcohol resin and allowed to cure in a nitrogen atmosphere with a metal halide lamp. An energy needed for each of the mixtures to cure is as shown in Table 2.

Each of the cured products was immersed in isopropyl alcohol for 10 hours; a 1:1 mixture of water/isopropyl alcohol for 10 hours; and then pure water for 20 hours. Subsequently, each of the immersed products was subjected to measurement of an oxygen permeability with a film oxygen permeability meter, ex Tsukuba Rika Seiki Co. The results are as shown in Table 2.

TABLE 2

|  | Ex. 1 | Ex. 2 | Ex. 3 | Ex. 4 | Ex. 5 | Com. Ex. 1 | Com. Ex. 2 |
|---|---|---|---|---|---|---|---|
| Compound | II | IV | V | VI | VII | VIII | XI |
| Energy needed for curing, mJ/cm$^2$ | 1200 | 1000 | 900 | 1700 | 2400 | 900 | 1000 |
| Oxygen permeability × 10$^{-11}$, 1) | 90 | 87 | 85 | 85 | 86 | 82 | 74 |

1): (cm$^2$/sec) [mlO$_2$/(ml · hPa)]

The present silicone compounds provide the cured products which have higher oxygen permeabilities, compared to the silicone compound of Comparison Example 1 (Tris-A) and the silicone compound of Comparison Example 2. The present silicone compounds have excellent compatibilities with other monomers and good reactivities.

INDUSTRIAL APPLICABILITY

The present silicone compound provides a cured product which has a higher oxygen permeability. The present silicone compound is liquid at room temperature and, therefore, easy to handle. Further, The present silicone compound has good reactivity. The present silicone compound is useful for ophthalmic device compositions, coatings and cosmetic compositions such as skin care cosmetics, hair care cosmetics, antiperspirants, deodorants, makeup cosmetics and ultraviolet protection cosmetics.

The invention claimed is:

1. A silicone compound represented by the following formula (1):

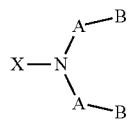

wherein
A is, independently of each other, a linear or branched divalent hydrocarbon group having 1 to 6 carbon atoms, in which hydrocarbon group one or more of the hydrogen atoms bonded to carbons atoms may optionally be replaced by, correspondingly, one or more halogen atoms, B is, independently of each other, a monovalent organosilicone residue having 2 to 20 silicon atoms, and X is a group represented by the following formula (4):

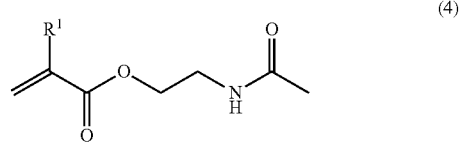

wherein R$^1$ is a hydrogen atom or a methyl group.

2. The silicone compound according to claim 1, wherein B is, independently of each other, a group represented by the following formula (2):

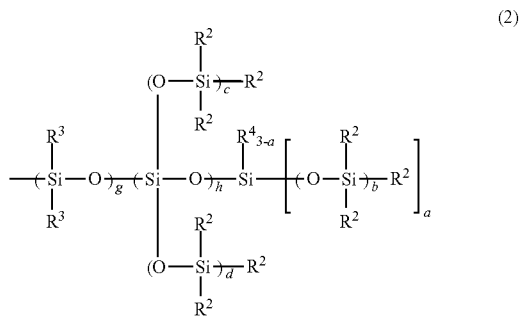

wherein R$^2$, R$^3$ and R$^4$ are, independently of each other, an alkyl group having 1 to 10 carbon atoms or an aryl group having 6 to 12 carbon atoms, b is an integer of from 1 to 3, c is an integer of from 1 to 3, d is an integer of from 0 to 3, g is an integer of from 0 to 10, h is an integer of from 0 to 2, and a is an integer of from 0 to 3, provided that not all of a, h and g are zero.

3. The silicone compound according to claim 2, represented by the following general formula (6):

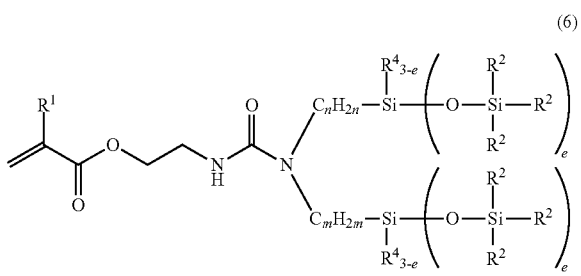

wherein R$^1$ is a hydrogen atom or a methyl group, R$^2$ and R$^4$ are, independently of each other, an alkyl group having 1 to 10 carbon atoms, n is an integer of from 1 to 6, m is an integer of from 1 to 6, and e is, independently of each other, 1, 2 or 3.

4. The silicone compound according to claim 3, wherein both n and m are 3.

5. The silicone compound according to claim 4, wherein R$^1$ is a hydrogen atom.

6. A method for preparing a silicone compound represented by the following general formula (1):

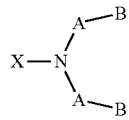
(1)

wherein
- A is, independently of each other, a linear or branched divalent hydrocarbon group having 1 to 6 carbon atoms, in which hydrocarbon group one or more of the hydrogen atoms bonded to carbons atoms may optionally be replaced by, correspondingly, one or more halogen atoms,
- B is, independently of each other, a monovalent organosilicone residue having 2 to 20 silicon atoms, and
- X is a group represented by the following formula (4):

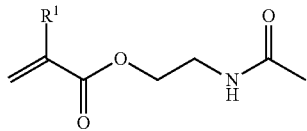
(4)

wherein $R^1$ is a hydrogen atom or a methyl group,
wherein the method comprises a step of reacting a compound represented by the following formula (8):

Y—Z (8)

wherein Y is a group represented by the following formula (4'):

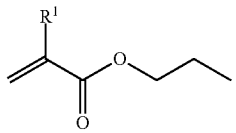
(4')

wherein $R^1$ is a hydrogen atom or a methyl group and Z is a halogen atom or a group which is reactive with an amine, with a compound represented by the following formula (9):

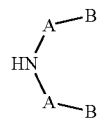
(9)

wherein A and B are as defined above.

7. The method according to claim 6, wherein the compound represented by the formula (8) is represented by the following formula (12):

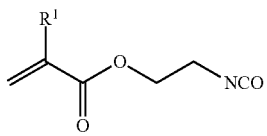
(12)

wherein $R^1$ is a hydrogen atom or a methyl group,
the compound represented by the formula (9) is represented by the following formula (13):

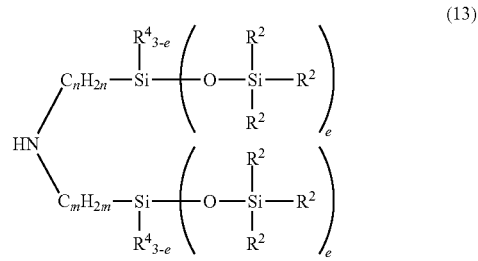
(13)

wherein $R^2$ and $R^4$ are, independently of each other, an alkyl group having 1 to 10 carbon atoms, n is an integer of from 1 to 6, m is an integer of from 1 to 6, e is, independently of each other, 1, 2 or 3, and
the silicone compound obtained is represented by the following formula (6):

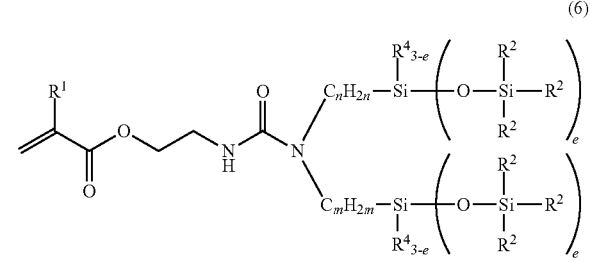
(6)

wherein $R^1$, $R^2$, $R^4$, n, m and e are as defined above.

8. The method according to claim 6 or the method according to claim 7, wherein $R^1$ is a hydrogen atom.

* * * * *